(12) United States Patent
Woods et al.

(10) Patent No.: US 8,904,919 B2
(45) Date of Patent: Dec. 9, 2014

(54) EXTENSILE FLUIDIC MUSCLE ACTUATOR (75) Inventors: Benjamin K. S. Woods, Baltimore, MD (US); Norman M. Wereley, Potomac, MD (US); Curt Kothera, Crofton, MD (US); Shane M. Boyer, Owings Mills, MD (US)

(73) Assignees: InnoVital Systems, Inc., Calverton, MD (US); University of Maryland, College Park, College Park, MD (US)

( * ) Notice: Subject to any disclaimer, the term of this patent is extended or adjusted under 35 U.S.C. 154(b) by 1023 days.

(21) Appl. No.: 12/955,242

(22) Filed: Nov. 29, 2010

(65) Prior Publication Data

US 2011/0067563 A1    Mar. 24, 2011

Related U.S. Application Data (63) Continuation-in-part of application No. 11/502,360, filed on Aug. 11, 2006, now Pat. No. 7,837,144, and a continuation-in-part of application No. 12/456,139, filed on Jun. 11, 2009, now Pat. No. 8,307,753.

(60) Provisional application No. 61/283,145, filed on Nov. 30, 2009.

(51) Int. Cl.
*F15B 15/10* (2006.01)
*A61F 2/08* (2006.01)
*A61F 2/50* (2006.01)

(52) U.S. Cl.
CPC ........... *A61F 2/08* (2013.01); *A61F 2002/5066* (2013.01); *A61F 2002/0894* (2013.01); *F15B 15/103* (2013.01)
USPC .......................................................... 92/92

(58) Field of Classification Search
CPC .................................................... F15B 15/103
USPC ........................................................ 92/89–92
See application file for complete search history.

(56) References Cited

U.S. PATENT DOCUMENTS

| | | | |
|---|---|---|---|
| 2,789,580 A | 4/1957 | Woods | |
| 2,844,126 A | 7/1958 | Gaylord | |
| 4,615,260 A | 10/1986 | Takagi | |
| 4,733,603 A | 3/1988 | Kukolj | |
| 4,751,869 A | 6/1988 | Paynter | |
| 4,860,639 A * | 8/1989 | Sakaguchi | 92/92 |
| 5,021,064 A | 6/1991 | Caines | |
| 5,158,005 A * | 10/1992 | Negishi et al. | 92/92 |
| 5,165,323 A * | 11/1992 | Sato | 92/92 |
| 6,223,648 B1 * | 5/2001 | Erickson | 92/92 |
| 6,349,746 B1 | 2/2002 | Bergemann | |
| 6,811,168 B2 * | 11/2004 | Acker et al. | 92/92 |
| 6,830,019 B2 * | 12/2004 | Kluge | 92/92 |

* cited by examiner

*Primary Examiner* — F. Daniel Lopez

(74) *Attorney, Agent, or Firm* — Ober, Kaler, Grimes & Shriver; Royal W. Craig (57) ABSTRACT An Extensile Fluidic Muscle Actuator (FMA) that changes the normal direction of force and motion, achieving compressive force generation and extensile motion output with just a small increase in friction, weight, and cost is disclosed. The motion conversion is accomplished by a pushrod that is attached to the inside end of one of the actuator's end fittings, and extends through the actuator body and slidably out through the other end fitting. The other end fitting is held stationary by a seal housing that contains a sealing element to retain internal fluid pressure as the actuator moves. A linear bearing may also be installed to keep the rod aligned and centered properly in the seal. Upon pressurization of the actuator, the flexible body of the actuator will expand radially, causing relative contractile motion between the two end fittings. However, as the two end fittings are drawn towards each other, the pushrod is extended.

27 Claims, 5 Drawing Sheets

EXTENSILE FLUIDIC MUSCLE ACTUATOR

CROSS-REFERENCE TO RELATED APPLICATION(S)

The present application derives priority from U.S. provisional application No. 61/283,145 filed 30 Nov. 2009, and is a continuation-in-part of U.S. application Ser. No. 11/502,360 filed Aug. 11, 2006 now U.S. Pat. No. 7,837,144, and a continuation-in-part of U.S. patent application Ser. No. 12/456,139 filed Jun. 11, 2009 now U.S. Pat. No. 8,307,753.

BACKGROUND OF THE INVENTION

1. Field of the Invention

The present invention generally relates to actuators used for performing mechanical work and, more particularly, to fluidic artificial muscles, artificial muscle actuators, or McKibben artificial muscles.

2. Description of Prior Art

Fluidic muscle actuators (also known as artificial muscle actuators, or McKibben artificial muscles, among other names) are simple mechanical actuators that harness pressurized fluid (air, water, oil, etc.) to generate significant forces and deflections. They have attracted interest in the fields of robotics, industrial automation, and recently aerospace engineering (U.S. patent application Ser. No. 11/502,360) because of their simple design, light weight, compliance, and excellent performance in terms of forces and deflections generated.

The operating principle of fluidic muscles is as follows. The inner elastic bladder is pressurized with the operating fluid (air, water, oil etc.), causing an inflation and expansion of the bladder. The braided sleeve around the bladder is thereby forced to expand; however, the fixed length of the stiff sleeve fibers generates either a tensile or a compressive force along the main axis of the actuator, in addition to relative motion between the two end fittings, either contraction or extension, but not both. The direction of force and motion are dependent on the initial angle between the filaments of the braided sleeve. Actuators with the filaments of the sleeve aligned primarily with the length axis of the actuator will be contractile. If the filaments of the sleeve are aligned primarily with the radial axis of the actuator, then the motion is extensile. There is a neutral braid angle in between these two extremes that is the cross-over point between these two regimes. Typically this angle has been found to be 54°44' as measured from the length axis of the actuator to the braid filaments. For a tension/contraction actuator, the bladder expansion is radial and for a compression/extension actuator, the bladder expansion is primarily axial. The direction of force and motion is inherent to the construction of a given actuator and can not be changed once the actuator is made. This force and motion is transferred to an external system via the end fittings.

Fluidic muscle actuators of this type have been known in prior patent publications. A related device was disclosed in April 1957 in U.S. Pat. No. 2,789,580. Many different designs have been disclosed over the years (U.S. Pat. Nos. 2,844,126, 4,733,603, 4,751,869, and 5,021,064). Some more recent designs, such as those disclosed in (U.S. Pat. Nos. 4,615,260 and 6,349,746 B1), are commercially available.

The vast majority of devices known in the prior art have the braided sleeve configured to generate tensile forces and contractile motions. This is partly because the tension force levels that can be generated in the contractile configuration are much larger than the compression forces generated with the alternate configuration.

However, for many current and future applications of these actuators, contractile motion is not preferred. For example, an industrial stamping process where an extensile actuator is needed to push two plates together, thereby creating a compressive force between them. If extensile motion such as this is desired, then current Fluidic Muscle Actuator designs become less attractive because they will either lose much of their force generation potential if an extensile braid angle configuration is used, or they will lose their simplicity advantage if some additional complex mechanism is needed to convert the motion of a contractile braid angle actuator into extensile output motion.

Therefore, what is desired is a new design of Fluidic Muscle Actuator which combines the high force capability of a contractile braided sleeve configuration with compressive force generation and extensile motion output. The current invention accomplishes this goal with a supplementary motion conversion package that can be added or removed from the actuator with little effort, and that changes the direction of force and motion with only a small increase in friction, weight, and cost.

SUMMARY OF THE INVENTION

In accordance with the foregoing objects, the present invention is a method and device for converting the output of a fluidic muscle actuator from contraction/tension to extension/compression. This device may either be an integral part of the actuator that is included as the actuator is assembled, or it may be a separate modular package that can be taken on and off depending on what direction of motion/force is required for a certain application. The fluidic muscle may be manufactured using a variety of techniques, although the preferred embodiment uses the swaging system described in co-pending U.S. patent application Ser. No. 12/456,139 for "Fluidic Artificial Muscle Actuator and Swaging Process Therefor." It is assumed that whatever manufacturing method is employed will have two end fittings as part of the design to seal off both ends of the active bladder/sleeve portion, and to transfer the force and motion to the mechanism or system being acted upon. In the preferred embodiment of the present invention, a pushrod is attached to the inside end of one of the actuator's end fittings. Hence, for the purpose of this disclosure, this end fitting will be referred to as the moving end fitting. The pushrod extends through the inside of the actuator and out through the other end fitting, which will be referred to herein as the fixed end fitting. The external end of the pushrod is provided with some means of attachment to the mechanism or component being acted upon. Attached to the fixed end fitting is a seal housing component that contains a sealing element of some form which slides along the pushrod and allows for the actuator to retain its internal fluid pressure as the actuator moves. On at least one side of this sealing element, a linear bearing may be installed to keep the rod aligned and centered properly in the seal. Upon pressurization of the actuator, the flexible body of the actuator will expand radially, causing relative contractile motion between the two end fittings. As the two end fittings are drawn towards each other, the pushrod, being of fixed length, will be forced to extend farther outside of the actuator through the fixed end fitting. If the actuator is supported by the end fitting with the rod seal, described above as the fixed end fitting, and by the external end of the pushrod, then pressurization of the actuator will result in an increase in the distance between the mounting points, and a compressive force generated between them. The area between the two end fittings of the actuator still contracts, but the pushrod and the specific mounting arrangement change this relative contraction into overall output extension. This is the mechanism by which this invention allows for the superior contraction/tension behavior of these fluidic actuators to be utilized as extension/compression. Alternatively, this same device could be attached to a fluidic muscle actuator which produces extension/compression due to the geometry of its braided sleeve, thereby converting it into a contraction/tension actuator.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 3A shows one embodiment with a two-part bolted seal housing; and the second embodiment shown in FIG. 3B employs a two-part threaded seal housing.

Additionally, FIG. 3C shows the embodiment from FIG. 3B in a pressurized state. Here the bladder and sleeve have expanded, and as a result, the end fittings have been drawn together, resulting in extension of the pushrod relative to the fixed end fitting.

DETAILED DESCRIPTION OF THE PREFERRED EMBODIMENTS

The present invention is an Extensile Fluidic Muscle Actuator (FAM) that achieves compressive force generation and extensile motion output with a supplementary motion conversion feature that changes the normal direction of force and motion with just a small increase in friction, weight, and cost.

Figure 1:
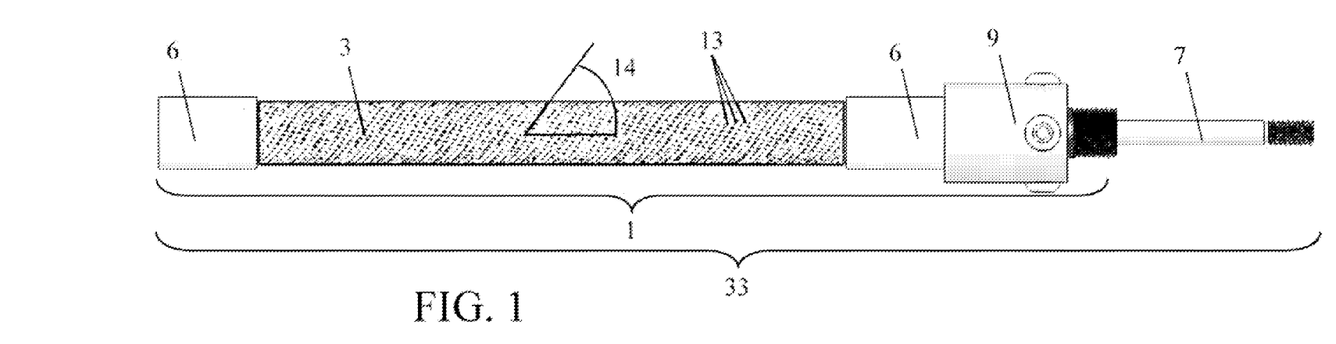
FIG. 1 shows an external side view of an embodiment of an Extensile Fluidic Muscle Actuator in a non-pressurized state.
Figure 2:
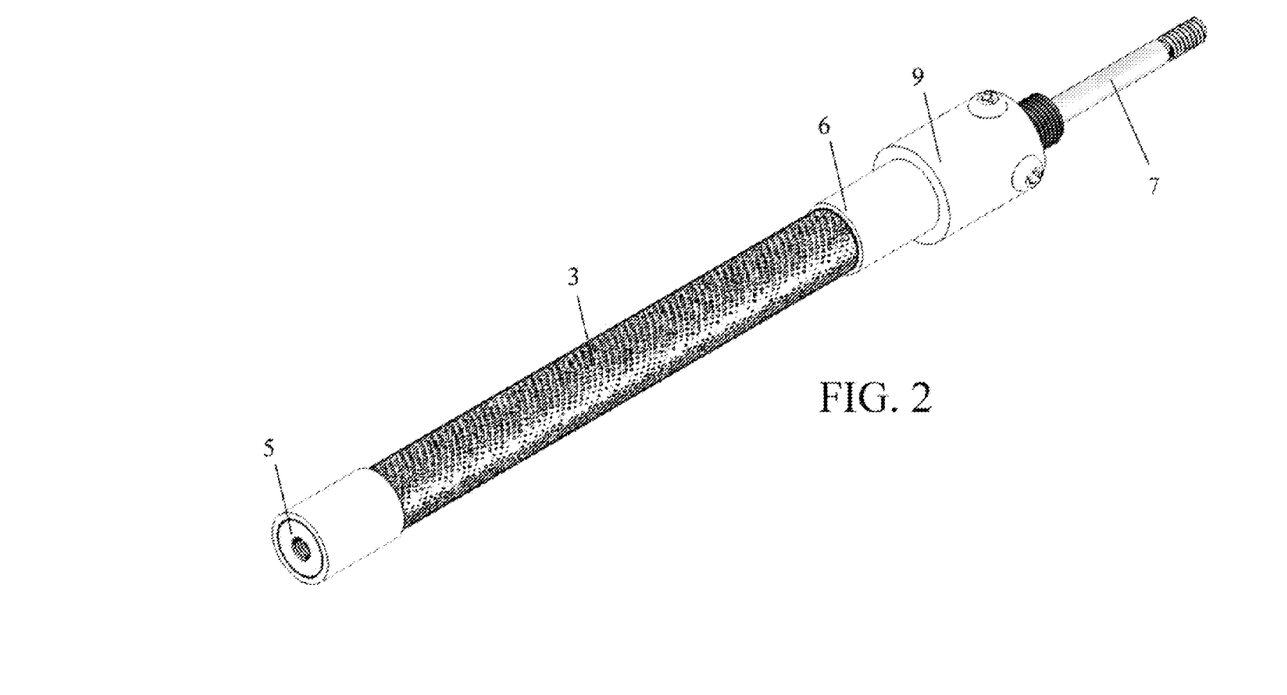
FIG. 2 is an external isometric view of an embodiment of an Extensile Fluidic Muscle Actuator in a non-pressurized state.
Figure 3:
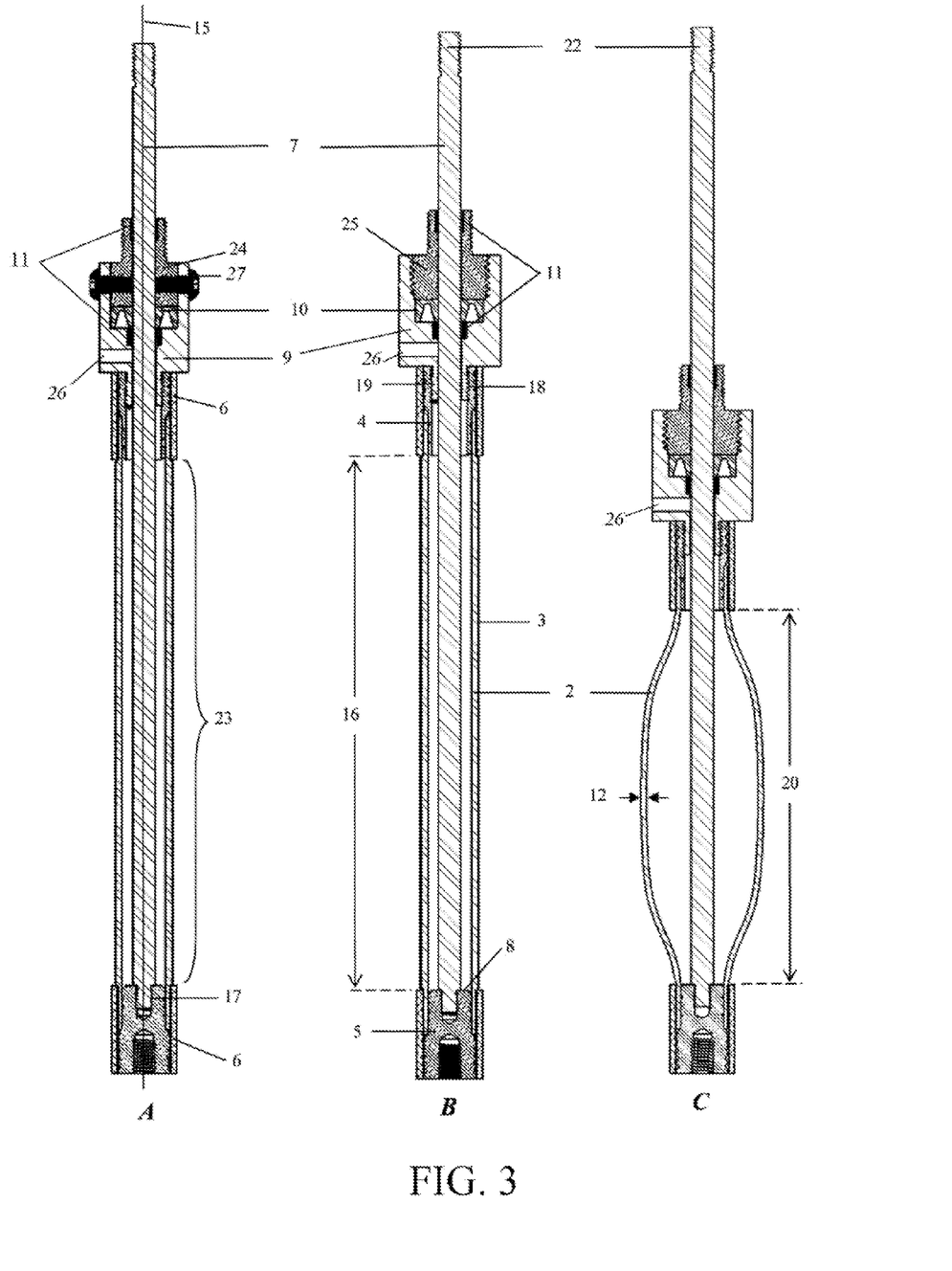
FIG. 3 shows cross section views of two of the embodiments of the invention.
Figure 4:
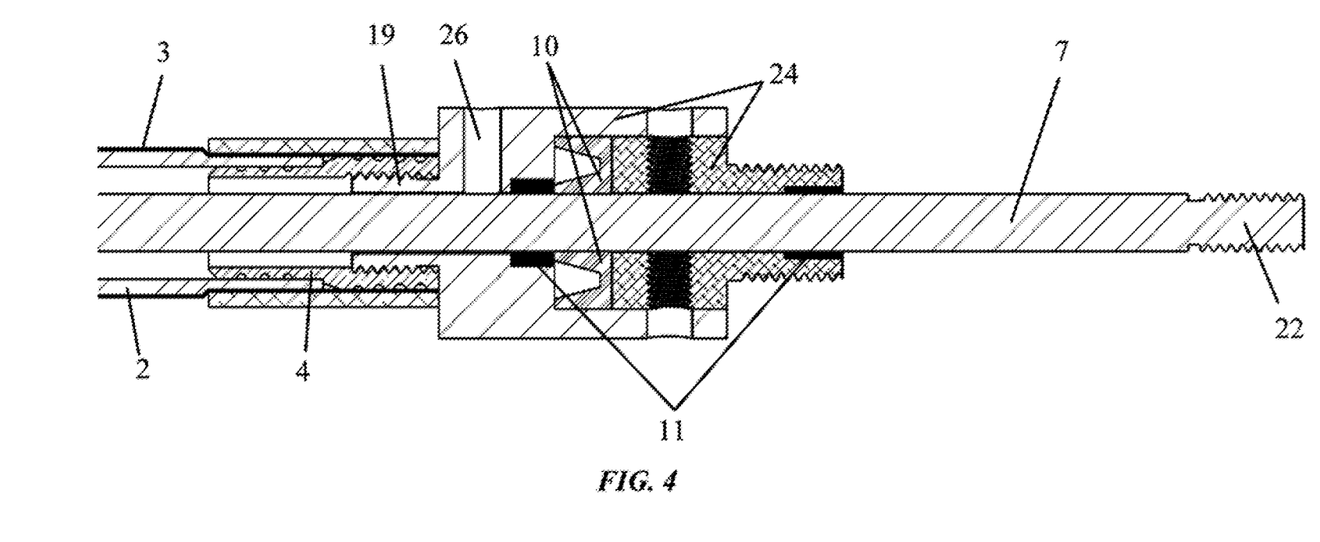
FIG. 4 provides a close-up cross section view of the seal housing and fixed end fitting region of one embodiment of the invention. This embodiment employs a fluid port integrated into the body of the seal housing.

FIGS. 1 and 2 show the Extensile Fluidic Muscle Actuator in a non-pressurized state. FIG. 3 is a cross section of the embodiment of FIGS. 1-2. With combined reference to FIGS. 1-2 and 3, the actuator body 1 comprises an elastic fluid bladder 2 surrounded by a stiff braided mesh sleeve 3. End fittings 4,5 are attached to each end to seal the bladder 2 and allow for connection of the actuator 33 to other components. In the preferred embodiment, a swage tube 6 is plastically deformed around the end fittings 4,5, braided sleeve 3 and bladder 2 to provide a fluid seal and a strong mechanical connection. This swaging process is described in full detail in copending U.S. patent application Ser. No. 12/456,139 for "Fluidic Artificial Muscle Actuator and Swaging Process Therefor." Any other conventional method of attaching these components could also be used with this invention, including hose clamps, crimping, wire winding, adhesive based approaches, etc.

Normally, when the elastic fluid bladder 2 is filled with fluid, the stiff braided sleeve 3 radially expands and axially contracts, yielding compressive and contractive force generation, respectively. However, the present invention accomplishes compressive force generation and extensile motion output with a direction change mechanism.

The direction change mechanism is attached to the actuator body via the two end fittings 4,5. One end fitting is designated the fixed end fitting 4, as it does not generally move upon pressurization of the actuator. The other end fitting is designated as the moving end fitting 5. As best seen in FIG. 3(A-C), pushrod 7 is affixed to the internal end 8 of the moving fitting 5. Pushrod 7 passes through a seal housing 9 which is attached to the fixed end fitting 4. The seal housing 9 contains at least one sealing element 10 which provides a pressure tight seal around the circumference of the pushrod 7. Additionally, linear bearings 11 may be included on one or both sides of the seal 10 to maintain alignment of the pushrod 7 relative to the seal housing 9. The pushrod 7 extends from its mounting point on the moving end fitting 5 through the entire internal length of the actuator body 1, through and then past the seal housing 9. The actuator 33 may be connected to the system or machine in which it is being employed via the pushrod and fixed end fitting 4/seal housing 9. With this arrangement, compressive force and extensile motion are created by the actuator 33 upon internal pressurization of the bladder 2. Specific details of the above-described components follow.

Bladder

The elastic fluid bladder 2 is preferably made from a low modulus, high strain elastic material, including, but not limited to, an elastomer or rubber. Silicone, polyurethane, and latex rubbers are the preferred materials, although any suitable material may be used without changing the invention. These materials allow for the large strains associated with pressurization, while minimizing the amount of energy required for their expansion. In the preferred embodiment, the bladder 2 is substantially cylindrical in shape, although other shapes of bladders can be used. Wall thickness 12 of the bladder 2 is chosen to ensure that the operating pressure can safely be maintained without rupture, when coupled with the braided sleeve 3. Additional wall thickness may or may not be desired to allow for material loss during long term actuation cycling due to braided sleeve 3/bladder 2 interactions, such as friction. Accordingly, the bladder 2 and/or braid 3 materials may be coated in a complementary material to reduce friction, heating, etc. Examples include, but are not limited to, PTFE, graphite, and dry film lubricants.

Braided Sleeve

The braided sleeve 3 preferably comprises a web of fiber filaments 13 that are braided in a helical fashion to form a sleeve that can expand or contract in diameter. While this is the preferred embodiment, the sleeve may alternatively be comprised of separate layers of helically wrapped filaments that are stacked instead of woven, where, in the case of two layers, the two individual layers encircle the bladder in opposing directions. In another embodiment, the filaments may be aligned with the length axis 15 of the actuator. These filaments could then be embedded into a soft (e.g. elastomer or rubber) matrix to maintain the spacing between fibers. Filament material can be any suitable high strength, high modulus material. Low friction and high wear resistance are also desirable in the braid material to reduce actuator self-heating and to extend fatigue life. Favored materials include, but are not limited to, aramid fibers, para-aramid, poly-p-phenylenebenzobisoxazole (PBO) fibers, carbon, or fiberglass fibers. Polymers such as Nylon, polyether ether ketone (PEEK), Polyester (PET), and Ultra High Molecular Weight Polyethylene (UHMWPE), etc. are also suitable. Metallic filaments (steel, stainless steel, titanium, etc.) can also be used, although they are not generally preferred. The sleeve filament density (distance between strands) and initial angle 14 of the braid 3 can be varied to influence the stiffness, force generation, deflection range, and other important actuator performance properties. Initial braid angle of the sleeve 14 is defined as the angle between a braid filament 13 and the longitudinal axis 15 of the actuator when the braid 3 is tight against the pressure bladder 2 and the actuator is at its resting length 16 (no internal pressure, no external loading).

End Fittings

The end fittings 4,5 are preferably constructed from a lightweight, but strong, material such as aluminum, titanium, plastic, fiber reinforced polymer, or similar. These can be machined, molded, or manufactured in any other way that allows for the necessary features and tolerances to be produced. The fittings 4,5 in the preferred embodiment shown include several features that are related to the aforementioned swaging manufacturing method. Also shown are the swage tubes 6 which clamp the bladder 2 and braided sleeve 3 onto the end fittings 4,5. The design features of the swage tubes 6 need not be described in detail as they are conventional components.

The moving end fitting 5 is provided with some means of attachment for the pushrod 7. For example, the pushrod 7 may be attached preferably to the center of the inside face of the internal end 8 of the moving fitting 5. In the shown embodiment, moving end fitting 5 is provided with a tapped hole 17 that allows the pushrod 7 to screw into the internal end 8 of the moving fitting 5. Preferably, this tapped hole 17 is of a smaller diameter than the pushrod 7, creating a step down in the diameter of the pushrod 7 that provides a mating face to ensure that the fitting 5 and pushrod 7 are parallel. Any other attachment means could be used instead of threading, including adhesive bonding, through pins, clips, etc. Alternatively, the pushrod 7 and moving fitting 5 could be manufactured as a single part. If desired, the pushrod 7 could be attached to the fitting 5 in a non-rigid manner. For example, a ball and socket joint or a universal joint could be integrated between the two, allowing angular rotation, but still transmitting the compressive forces. Such an approach might be useful if lateral loads or moments on the actuator 33 needed to be accommodated.

The fixed end fitting 4 can be of two basic designs, one that is designed to connect to a separate external seal housing 9 (as shown), or one that is integrally formed with the seal housing 9.

In the embodiments shown in FIG. 3, the seal housing 9 is an external component that attaches to the fixed end fitting 4. Many options exist for the attachment between these components, although it is necessary that the pushrod 7 be able to travel through the fitting 4 and into the seal housing 9 without interference. The embodiment shown incorporates a threaded hole 18 of large enough diameter that the hollow threaded extension of the seal housing 19 can have sufficient strength to handle the actuation forces, while the hole into the seal housing is large enough to provide clearance for the pushrod 7. Alternatively, the body of the end fitting 4 could be extended past the end of the swage tube 6 and the exposed external surface could be given threads or any other means of attachment to the seal housing 9.

The fixed end fitting 4 can also be designed to accommodate the seal housing 9 internally. If the direction change mechanism is a removable unit, then the seal housing 9 can be sized to fit inside of the end fitting 4 and be attached in a manner as to allow installation and removal of the direction change mechanism at will. If a permanent direction change mechanism were desired, the components and features of the seal housing 9 could be integrated into the design of the fixed end fitting 4 such that the two functions are performed by a single component.

Pushrod

The pushrod 7 is designed to carry the actuation forces from the moving end fitting 5 to the system or machine into which the actuator 33 is installed. Therefore, it must be made from a suitably strong and stiff material. Metals or composite materials are preferred. The loading is primarily compressive, so compressive strength and critical buckling load of this component are paramount. The critical buckling load of the pushrod 7 can be increased without increasing its weight by using a tube instead of a solid rod.

It is preferred that the portion of the pushrod 7 that comes in contact with the pressure seal 10 and the optional linear bearings 11 in the seal housing 9 have mechanical properties amenable to use with such components. Examples of properties that may be desired include high surface hardness, good wear resistance, low surface roughness, and low friction. Two preferred materials for obtaining these properties include heat treated metals and ceramics. The pushrod 7 could be made entirely from such materials, or if a lighter weight option were desired, bearing surface sleeves made from these high hardness materials could be installed around a pushrod made from a lighter material. For example, a heat-treated, precision ground 17-4PH stainless steel, thin-walled tube can be bonded to the outside of a carbon fiber/epoxy rod or tube. Fluidic muscle actuators typically have maximum strokes 20 on the order of 25-40% of their resting active length 16. For this reason, it is not necessary that a bearing surface sleeve cover the entire length of the pushrod 7. All that is required is to cover the portion that comes in contact with the seals 10 and bearings 11.

The external end 22 of the pushrod 7 may include some means of connection (such as threads as shown, rod end bearings, through holes, snap rings, etc.) for ease of integration and force transfer. While any such feature is within the scope of this invention, a modular approach is preferred. For example, the end of the pushrod 22 may be supplied with a specified standard size of male thread. An adapter block having the female equivalent threads on one side can be screwed thereto, and the adapter block may have any number of different features on the other side as a matter of design choice. This would simplify adaptation of the actuator 33 to different systems or different attachment schemes within the same system. For example, adapter blocks could be provided with different sized male or female threads, through holes, clevis pins, rod end bearings, snap rings, plain bearings, etc. This would eliminate the need to replace or modify the pushrod 7 whenever changes to the mounting scheme were desired.

Figure 5:
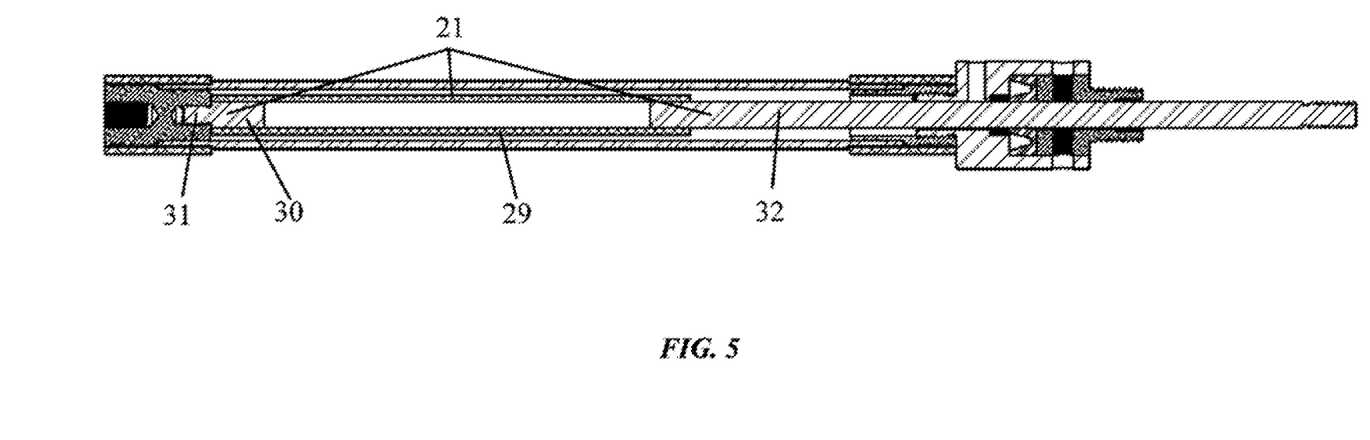
FIG. 5 shows a cross section side view of an embodiment of the invention employing a pushrod constructed from multiple parts.
Figure 6:
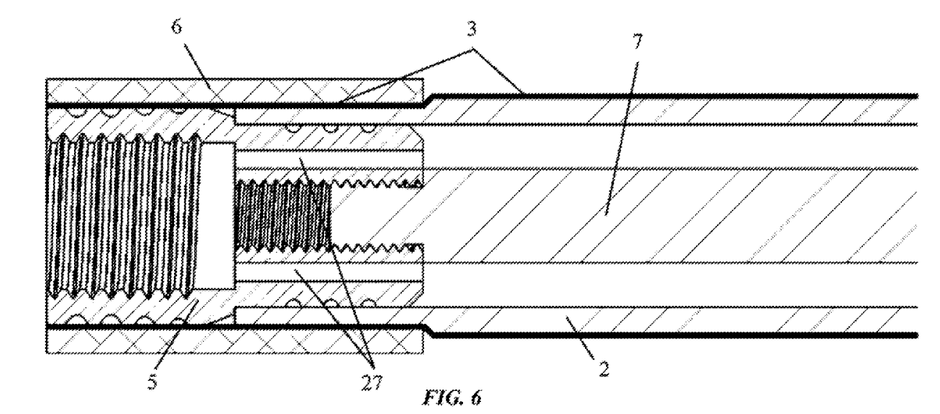
FIG. 6 shows a close-up cross section view of the moving end of an embodiment of an Extensile Fluidic Muscle Actuator which employs fluid ports integral to the moving end fitting.

The pushrod 7 may be a single part or alternatively may be made of any number of separate parts that combine to perform the functions described herein. Constructing the pushrod 7 from multiple parts gives more flexibility to its design and allows different portions of the components to be optimized to perform different functions. As one of many examples, the multi-part pushrod 21 shown here is made by combining a tube 29 with two rod segments 30,32. The tube portion 29 gives high buckling strength and large volume fill for the portion of the pushrod that stays internal to the actuator over the full deflection range. One of the rod segments 30 allows for attachment to the moving end fitting 5, preferably via a threaded extension 31. The second rod segment 32 allows for effective sealing and attachment to the external system.

Seal Housing

The seal housing 9 contains the components needed to allow the pushrod 7 to slide in and out of the actuator body 1 with minimal loss of the pressurized actuating fluid, and to do so with minimal friction. The primary component needed to perform this function is a sealing element 10 of some form. Any suitable single acting or double acting seal may be used, with the exact geometry and materials used being optimized for the operating fluid, pressure levels, and external environmental factors expected. In the shown embodiment, a symmetrical Buna-N rubber U-cup rod seal is used. Other preferred embodiments include, but are not limited to, Rod Hat seals, V-Packing seals, Rod T seals, and O-rings. Preferred materials for the seal 10 include natural, polyurethane, and silicone rubbers, as well as polytetrafluoroethylene (PTFE) and similar low friction materials.

In addition to the sealing element 10, it may be desirable to include linear bearings 11 into the seal housing 9 to help maintain alignment of the pushrod 7 relative to the seal 10. Linear bearings are particularly well suited to applications where pushrod alignment is critical, or where significant lateral (perpendicular to the pushrod) forces are expected. A single linear bearing can be installed on either side of the sealing element 10, or two or more can be included, with at least one on either side of the seal to better maintain alignment through the seal. In the preferred embodiment shown, one plain linear bearing is installed on either side of the seal 10. Preferred materials for these bearings include high strength, low friction polymers (Nylon, PEEK, Roulon, Vespel Etc.) or composite materials that provide the required strength and low friction by combining two or more different materials. PTFE lined aluminum and glass fiber filled PTFE are two preferred composite material bearing solutions. Metallic bearings are also an option, although they are not preferred. Alternatively, if the seal housing 9 were made from a suitable material, plain linear bearings could be included as integral features of the housing itself. For example, the housing 9 could be machined or molded from high strength, low friction polyetheretherketone (PEEK), with precise linear bearing features included into the machining process or in the mold.

Careful material selection for the seal housing 9 is critical to successful design of the component. In the embodiment shown, the seal housing 9 is a primary structural component that must carry the actuation loads between the active region of the fluidic muscle 23 and the structure or machine into which the actuator 33 is mounted. For this reason the material used for its construction must be suitably strong. For high cycle applications, the fatigue resistance of the seal housing, and of all other components, may also be an important design consideration. Expected operating temperatures will also guide material selection. Finally, manufacturing cost is also an important material selection driver. The preferred materials include metals (steel, aluminum, magnesium, etc.), polymers, and fiber reinforced polymers.

An optional addition to the invention that may be useful in particularly dirty operating environments is a shaft wiper around the pushrod 7. This would be installed such that it wiped the external portion of the pushrod clean as the pushrod 7 contracted back into the body of the actuator 1, thereby limiting the exposure of the linear bearings 11 and the seal 10 to dirt, grit, abrasive particles, or anything else that might reduce their effectiveness and life cycle duration. This component can be included into the seal housing 9 or can be installed separately.

In the embodiments shown, the sealing element 10 is contained within the seal housing 9 by a seal retainer 24,25 that is designed to be easily separated, facilitating installation and removal of the seal 10 and/or the linear bearings 11. When assembled, the seal retainer 24,25 and seal housing 9 hold the seal 10 completely captive, such that its alignment is maintained and it is unable to migrate or leave the body of the actuator 1. Thus, one of the multiple functions of the combination of seal housing 9 and seal retainer 24,25 is similar to that of a two-piece gland. Two different means of creating such a multiple part seal housing are shown in FIG. 3. At FIG. 3(A), one embodiment 24 uses screws to attach the seal retainer 24 to sealing element 10. At FIG. 3(B), another embodiment 25 has the two parts thread into each other. These are only two of many possible solutions, and the invention is not intended to be limited to these specifically noted embodiments. The invention encompasses any appropriate method of designing and fabricating the seal housing 9, whether it be a single part, multiple parts, or an integral part of the end fittings as discussed earlier.

Fluid Port

In order for the actuator 33 to operate, it is necessary to have at least one fluid port which allows for flow of the operating fluid, resulting in pressurization or exhaustion of the actuator. This feature is mentioned separately from the above components because it may be incorporated into the actuator 33 at many different places. The fluid port can be anything that connects the inside of the active portion of the actuator to a source of pressurized fluid. The port must be designed such that it can be effectively sealed to prevent pressure loss. Two different embodiments are shown here as examples. The embodiments shown in FIG. 3(A-C) have the fluid port 26 as part of the seal housing 9. In this case, a pressure fitting would be connected to the shown port 26 to allow for attachment to any manner of fluid piping system. This embodiment allows for the fluid piping to remain stationary as the fluidic muscle 33 is actuated.

Figure 7:
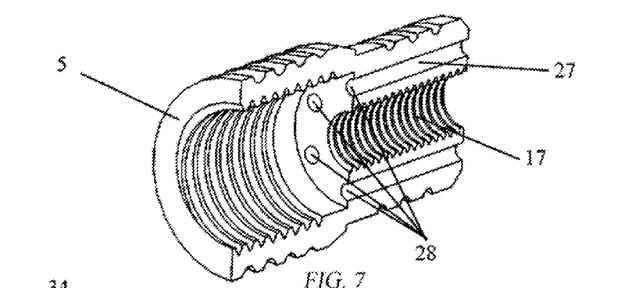
FIG. 7 shows an isometric cross section view of one embodiment of a moving end fitting with integral fluid ports

Another embodiment shown in FIG. 7 has a threaded fluid port 27 integral to the moving end fitting 5. In this case, the pressure fitting connects directly to the moving end fitting 5 and the fluid piping provides sufficient slack to move with the end fitting as the muscle 33 is actuated. An important feature of this embodiment is the passage by which the pressurized fluid is able to travel through the end fitting 5 and into the interior of the actuator. It is important that the material removed to allow passage of the fluid does not interfere with the ability of the end fitting 5 to attach to the pushrod 7 and transfer loads through it. One of many possible solutions is shown here. A radial pattern of through-holes 28 allows passage of the fluid while maintaining a web of material through which the actuation loads can be transferred from the moving end fitting 5 to the pushrod 7. The radial pattern of fluid ports 28 allows for fluid flow from the open end of the end fitting 5 into the internal portion of the actuator, while retaining sufficient material connection between the pushrod 7 mounting point and the end fitting to transfer the actuation loads from the bladder/braided sleeve/moving end fitting assembly into the pushrod.

Many other options exist for placement of the fluid port, including, but not limited to, the fixed end fitting 4, the end of a hollow pushrod, etc. Additionally, multiple fluid ports could be included into the actuator. For instance, a dedicated fluid fill port could be included into the seal housing 9 or fixed end fitting 4, and a dedicated fluid exhaust port could be included into the moving end fitting 5, or vice versa. Any number or combination of ports could also be used to increase fluid flow rates into and out of the actuator.

Outer Casing

Figure 8:
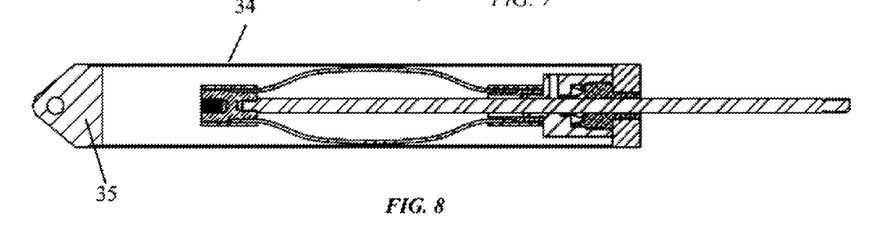
FIG. 8 shows a cross section view of one potential embodiment which includes an outer casing around the fluidic muscle actuator.

FIG. 8 shows a cross section view of an embodiment which includes an outer casing around the fluidic muscle actuator. Outer casing 34 is an optional feature which surrounds the fluidic muscle actuator. The casing attaches to the actuator at the fixed end, either to the seal housing 9, the swage tube 6, the fixed end fitting 4, or by some other means. The length of this tubular casing then extends over the fluidic muscle actuator. This casing may be provided with a casing end fitting 35, which serves as a mounting point for the actuator (into the system or machine in which it operates). In this embodiment, mounting the actuator at the casing end fitting 35 and at the end of the pushrod 7 will provide the desired reversal of the actuator force and displacement. This casing may also be used without such an end fitting as a means of protecting the fluidic muscle actuator. In this instance, it may still be desirable to have an outer casing end fitting 35 of some form to seal the open end of the outer casing 34.

Figure 9:
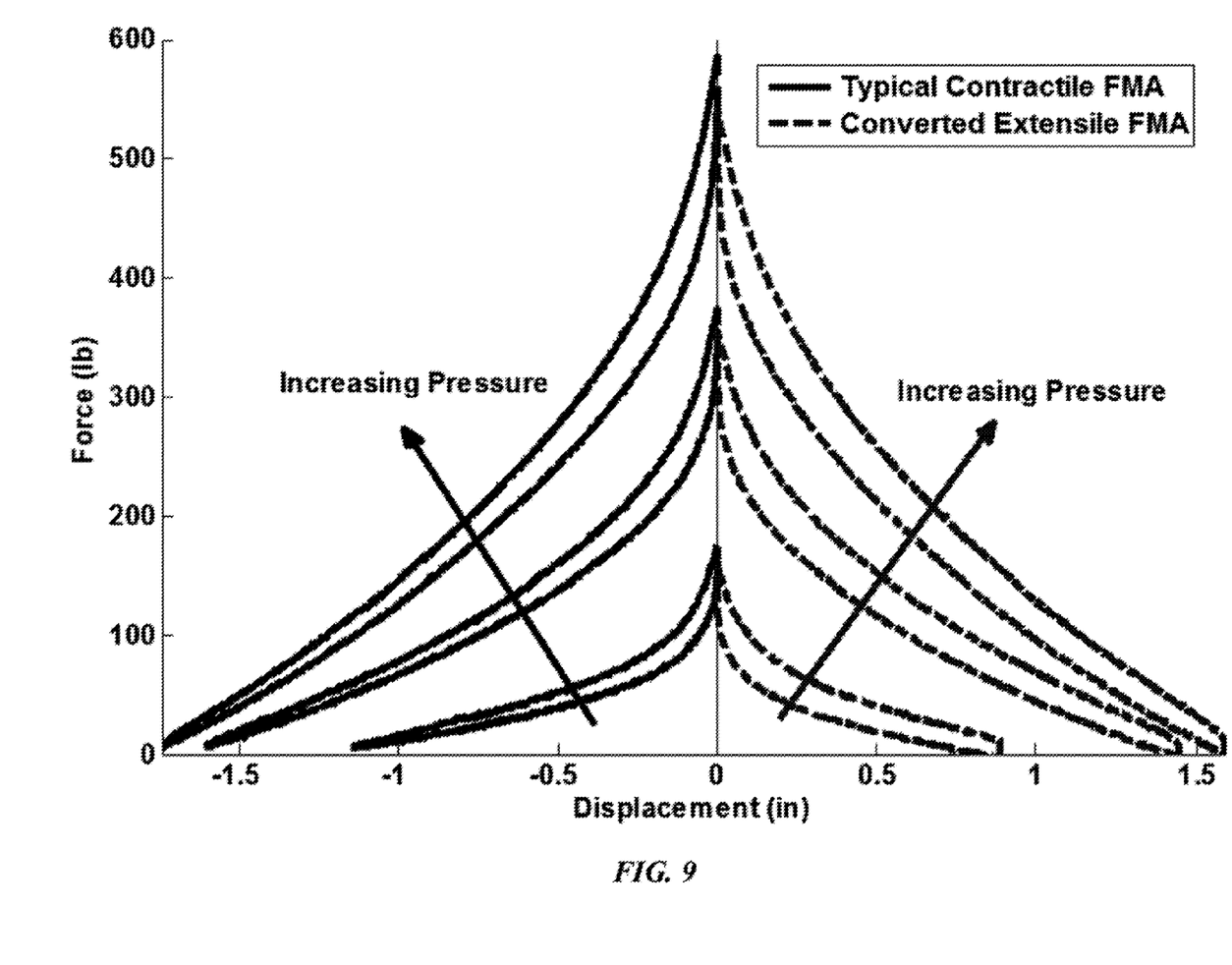
FIG. 9 shows the experimentally measured force versus displacement behavior of an extensile fluidic muscle actuator according to the present invention.

FIG. 9 shows the experimentally measured force versus displacement behavior of an extensile fluidic muscle actuator as described above. The extensile behavior of the actuator is shown at three different internal operating fluid pressures. Increasing pressure increases force and displacement. The contractile behavior of the same fluidic muscle tested without the displacement conversion device detailed in this invention is also shown here. The magnitudes of force and displacement are similar, showing the effectiveness of this device.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

What is claimed is:

1. A contractile fluidic muscle actuator, comprising:
a resilient bladder having two opposing open ends, a braided reinforcing mesh surrounding said resilient bladder and having two opposing open ends corresponding to said opposing open ends of said resilient bladder, said braided reinforcing mesh comprising filaments wound with a predetermined initial braid angle to produce extension between said first end fitting and said second end fitting upon internal fluid pressurization,
a first end-fitting sealingly affixed to one open end of said resilient bladder and braided reinforcing mesh;
a second end-fitting sealingly affixed to the second open end of said resilient bladder and braided reinforcing mesh;
a stationary seal housing attached to the second end fitting and adapted for attachment to a supporting structure;
a pushrod attached to said first end fitting and slidably passing through said second end fitting and seal housing;
a sealing element seated in said seal housing and providing a pressure tight seal circumferentially around the pushrod; and
a port for allowing a flow of pressurized fluid into and out from said resilient bladder; whereby when an internal pressure within said resilient bladder is increased, said pushrod retracts; whereby said pushrod effectively becomes a pullrod; and
wherein said pushrod comprises multiple discrete parts.

2. An extensile fluidic muscle actuator, comprising:
a resilient bladder having two opposing open ends, a braided reinforcing mesh surrounding said resilient bladder and having two opposing open ends corresponding to said opposing open ends of said resilient bladder, said braided reinforcing mesh translating fluid expansion of said resilient bladder into axial contraction;
a first end-fitting sealingly affixed to one open end of said resilient bladder and braided reinforcing mesh;
a second end-fitting sealingly affixed to the second open end of said resilient bladder and braided reinforcing mesh;
a stationary seal housing attached to the second end fitting and adapted for attachment to a supporting structure;
a pushrod made from a tubular hollow cross section attached to said first end fitting and slidably passing through said second end fitting and seal housing and adapted for external attachment for force transfer;
a sealing element seated in said seal housing and providing a pressure tight seal circumferentially around the pushrod; and
a port for allowing a flow of pressurized fluid into and out from said resilient bladder;
whereby when an internal pressure within said resilient bladder is increased, said pushrod extends.

3. An actuator as in claim 2, further comprising a linear bearing seated in said seal housing and abutting said pushrod to facilitate sliding.

4. An actuator as in claim 2, wherein the pushrod is a single solid piece that attaches on one end to the first end fitting and on its other end to the system or machine in which the actuator is installed.

5. An actuator as in claim 2, wherein the pushrod comprises multiple discrete parts.

6. An actuator as in claim 5, wherein a portion of the pushrod internal to the resilient bladder reduces the internal air volume that is required to be filled during pressurization.

7. An actuator as in claim 5, wherein a portion of the pushrod is covered with a coating or sleeve for optimal surface contact properties with the seal and/or bearings.

8. An actuator as in claim 2, wherein one end of the pushrod is threaded for attachment.

9. An actuator as in claim 2, wherein the pushrod and said first end fitting comprises a single unitary component.

10. An actuator as in claim 2, wherein the second end fitting is attached to said supporting structure.

11. An actuator as in claim 2, further comprising a pushrod shaft wiper component that removes foreign material from the surface of the pushrod.

12. An actuator as in claim 2, wherein said seal housing comprises a removable seal retainer to allow access to internal components during assembly and/or during maintenance.

13. The actuator of claim 2, wherein said seal housing comprises any one from among the group of integral bearing, sealing, and/or wiping elements.

14. The actuator of claim 2, wherein said seal housing incorporates a fluid port to allow for pressurizing and exhausting of the actuator.

15. The actuator of claim 2, wherein said second end fitting comprises a fluid port to allow for pressurizing and exhausting of the actuator.

16. The actuator of claim 2, wherein one of said end fittings incorporates said fluid port to allow for pressurizing and exhausting of the actuator.

17. An actuator as in claim 2, comprising a plurality of fluid ports to increase the maximum flow rate of fluid into and out of the actuator.

18. An actuator as in claim 2, wherein said end fittings are attached to the braided sleeve and the resilient bladder by any one from among a group consisting of swaging, hose clamps, wire wrapping, press fitting, and adhesive bonding.

19. An actuator as in claim 2, wherein the braided sleeve is embedded in said resilient bladder.

20. An actuator as in claim 2, wherein said braided reinforcing mesh comprises filaments wound with a predetermined initial braid angle to produce contraction between said first end fitting and said second end fitting upon internal fluid pressurization.

21. An actuator as in claim 2, which also includes an outer casing component around the fluidic muscle actuator.

22. An actuator as in claim 2, which also includes an outer casing component around the fluidic muscle actuator and an outer casing end fitting to provide a means for installation.

23. An extensile Fluidic Muscle Actuator (FMA) that translates increasing internal pressure into extensile motion, comprising:
 an elastic fluid bladder having two open ends;
 a sleeve formed of a mesh of fibers encircling said fluid bladder; a fixed end fitting inserted into one of the open ends of said elastic fluid bladder;
 a movable end fitting inserted into another of the open ends of said elastic fluid bladder;
 a first swage tube plastically deformed about the fixed end fitting, mesh sleeve, and bladder to provide a first fluid seal;
 a second swage tube plastically deformed about the movable end fitting, mesh sleeve, and bladder to provide a second fluid seal;
 a pushrod attached to the movable end fitting and extending centrally through said elastic fluid bladder and sleeve, and slidably outward through said fixed end fitting;
 whereby internal fluid pressurization within said fluid bladder causes radial expansion thereof within said sleeve, causing axial contraction of said sleeve and fluid bladder, and axial extension of said pushrod relative to the fixed end fitting; and
 wherein said pushrod is made from a tubular hollow cross section.

24. The extensile FMA according to claim 23, further comprising a port for allowing a flow of pressurized fluid into and out from said fluid bladder.

25. The extensile FMA according to claim 24, wherein said pushrod is integrally formed with said movable end fitting.

26. The extensile FMA according to claim 23, further comprising a sealing element encircling said pushrod within said fixed end fitting for maintaining internal fluid pressure within said bladder as the pushrod moves through said fixed end fitting.

27. The extensile FMA according to claim 23, wherein the fixed end fitting is attached to a supporting structure.

* * * * *